(12) United States Patent
Auguste et al.

(10) Patent No.: US 8,246,970 B2
(45) Date of Patent: Aug. 21, 2012

(54) WATER-IN-OIL SOLID EMULSION-TYPE COSMETIC COMPOSITIONS

(75) Inventors: Frederic Auguste, Chevilly-Larue (FR); Emmanuelle Portois, Chatillon (FR)

(73) Assignee: L'Oreal, Paris (FR)

( * ) Notice: Subject to any disclaimer, the term of this patent is extended or adjusted under 35 U.S.C. 154(b) by 1244 days.

(21) Appl. No.: 10/834,918

(22) Filed: Apr. 30, 2004

(65) Prior Publication Data

US 2004/0223989 A1 Nov. 11, 2004

Related U.S. Application Data

(60) Provisional application No. 60/470,868, filed on May 16, 2003.

(30) Foreign Application Priority Data

Apr. 30, 2003 (FR) ...................................... 03 05326

(51) Int. Cl.
*A61K 8/02* (2006.01)
*A61K 8/25* (2006.01)
(52) U.S. Cl. ..................................................... 424/401
(58) Field of Classification Search .................. None
See application file for complete search history.

(56) References Cited

U.S. PATENT DOCUMENTS

| 5,814,322 A | * | 9/1998 | Sebillotte-Arnaud | ........ | 424/401 |
| 5,830,486 A | * | 11/1998 | Nanba et al. | .................. | 424/401 |
| 5,876,704 A | | 3/1999 | Collin et al. | | |
| 7,037,511 B1 | | 5/2006 | Gers-Barlag et al. | | |
| 2001/0055580 A1 | * | 12/2001 | Belli et al. | ................. | 424/70.16 |
| 2002/0009471 A1 | * | 1/2002 | Yamasaki et al. | ............. | 424/401 |
| 2002/0106385 A1 | * | 8/2002 | Vatter et al. | ................... | 424/401 |

FOREIGN PATENT DOCUMENTS

| EP | 0 374 332 A1 | | 6/1990 |
| EP | 0374322 | * | 6/1990 |
| JP | S64-079104 | | 5/1989 |
| JP | A-10-114625 | | 5/1998 |
| JP | A-11-236308 | | 8/1999 |
| JP | A-2001-072528 | | 3/2001 |
| JP | 2001-261519 | | 9/2001 |

OTHER PUBLICATIONS

Dow Corning, "Dow Corning(r) 2501 Cosmetic Wax" Jul. 23, 2001.*
Dow Corning. "Dow Corning Silicone Emulsifiers," 2002.
Dow Corning. "Dow Corning® 2501 Cosmetic Wax," Jul. 23, 2001.
"Wacker-Belsil® DMC 6038-Bis-PEG 15 Methyl Ether Dimethicone," Wacker-Belsil, Feb. 1, 2006.
Bolden, Renee Ph.D. "Optical Microscopy Evaluation of Wax Raw Materials,", 2004.

\* cited by examiner

*Primary Examiner* — Brian Gulledge
(74) *Attorney, Agent, or Firm* — Oliff & Berridge, PLC

(57) ABSTRACT

A cosmetic composition in the form of a water-in-oil solid emulsion includes an aqueous phase dispersed in a fatty phase, wherein the fatty phase includes at least one wax whose melting point is between 25° and 42° C., which is in solid form in the form of crystallites with a shape factor at least equal to 2.

29 Claims, No Drawings

WATER-IN-OIL SOLID EMULSION-TYPE COSMETIC COMPOSITIONS

CROSS-REFERENCE TO RELATED APPLICATIONS

This application claims the benefit of French Application No. 03 05326 filed on Apr. 30, 2003 and U.S. Provisional Application No. 60/470,868 filed on May 16, 2003, the entire disclosures of which are incorporated by reference herein.

BACKGROUND OF THE INVENTION

The present invention relates to the field of water-in-oil solid emulsions for caring for and/or treating and/or making up human skin, including the scalp, and/or the lips, which are especially in the form of a cast makeup product and in particular a makeup stick such as lipsticks or foundations. They may especially be makeup and/or care compositions for the skin and/or the lips, antisun compositions and hygiene compositions, for instance deodorants.

In the cosmetics field, water-in-oil emulsions are commonly used since they especially allow active agents to be conveyed in the aqueous phase and give a sensation of freshness during and after application. Conventional water-in-oil emulsions contain one or more surfactants and an oily phase. They may also comprise a waxy phase. The waxy phase serves especially to structure the water-in-oil emulsion in order especially to obtain a stick therefrom. To do this, the wax particles create between themselves a network established by connecting the wax particles together, and it is this network that gives the product cohesion.

In general, conventional solid water-in-oil emulsions cannot contain a high proportion of aqueous dispersed phase, i.e., more than 50% by weight, without the risk of significantly impairing the expected mechanical properties.

Thus, patent application EP 1 064 908 describes solid cosmetic compositions of inverse emulsion type containing less than 30% by weight of water stabilized with an emulsifier from the carboxy-alkyl-polyglycerol family, and a fatty phase whose liquefaction point is greater than 60° C. Patent application JP-A-03 261 707 describes solid cosmetic emulsions containing silicone oils, waxes with a melting point equal to 80° C., water and at least one emulsifier of dimethicone copolyol type. Patent application WO 99/47111 describes solid cosmetic compositions of the water-in-oil emulsion type comprising less than 40% by weight of an aqueous phase emulsified using a silicone surfactant of alkyldimethicone copolyol type, in a fatty phase containing a polyethylene wax and a hydrogenated jojoba wax, the melting points of which are about 70° C.

More recently, patent application EP 1 159 954 proposes the use, in solid inverse emulsions, of hydrogenated jojoba wax as a dispersion in an aqueous phase, present in a proportion of from 5% to 50% by weight, the emulsion being stabilized with at least one silicone surfactant of polyoxyalkylene type.

SUMMARY OF THE INVENTION

Unexpectedly, the inventors have found that it is possible to use effectively, as texturing agent in a solid water-in-oil emulsion, a specific wax characterized by its melting point and its ability to be at room temperature in the form of crystallites of specific shape. Advantageously, such a wax allows the production of cosmetic compositions in the form of sufficiently hard non-brittle sticks up to very high aqueous phase contents. The corresponding compositions also allow sufficient deposition on keratin materials.

In various exemplary embodiments, the present invention includes a cosmetic composition in the form of a water-in-oil solid emulsion comprising an aqueous phase dispersed in a fatty phase, wherein the fatty phase comprises at least one wax whose melting point is between 25° C. and 42° C., and which is in solid form in the form of crystallites with a shape factor at least equal to 2.

In various exemplary embodiments, the present invention includes methods in which at least one wax with a melting point of between 25° C. and 42° C., which is in solid form in the form of crystallites with a shape factor at least equal to 2, is employed as a texturing agent for the preparation of a cosmetic composition in the form of a water-in-oil solid emulsion.

In various exemplary embodiments, the present invention includes methods in which at least one wax which is in solid form in the form of crystallites with a shape factor at least equal to 2, is employed as a texturing agent for the preparation of a cosmetic composition in the form of a water-in-oil solid emulsion containing more than 50% by weight of an aqueous phase.

In various exemplary embodiments, the present invention includes a cosmetic process for caring for and/or making up the skin and/or the lips, comprising the application to the skin and/or the lips of a composition in accordance with the invention.

In various exemplary embodiments, the compositions according to this invention are water-in-oil emulsions, i.e., emulsions obtained by the emulsification, using one or more surfactants, of an aqueous phase in an oily phase.

DETAILED DESCRIPTION OF EXEMPLARY EMBODIMENTS

For the purposes of the invention, the term "texturing agent" denotes a compound or mixture of compounds that allows a solid emulsion to be obtained.

The term "solid" means that the measurement of the maximum force measured by texturometry during the penetration of a probe into a formulation sample should be at least equal to 0.25 newtons, in particular at least equal to 0.30 newtons and especially at least equal to 0.35 newtons, evaluated under specific measuring conditions as follows.

The formulations are cast while hot into jars 4 cm in diameter and 3 cm deep. Cooling is performed at room temperature. The hardness of the formulations prepared is measured after waiting for 24 hours. The jars containing the samples are characterized in texturometry using a texturometer such as the machine TA-XT2 sold by the company Rheo, according to the following protocol: a probe of stainless-steel ball type 5 mm in diameter is brought into contact with the sample at a speed of 1 mm/sec. The measuring system detects the interface with the sample with a detection threshold equal to 0.005 newtons. The probe penetrates 0.3 mm into the sample, at a speed of 0.1 mm/sec. The measuring machine records the change in force measured in compression over time, during the penetration phase. The hardness of the sample corresponds to the mean of the maximum values of the force detected during penetration, over at least three measurements.

As specified previously, the inventors have found that the incorporation into water-in-oil emulsions of at least one wax in accordance with the invention makes it possible simultaneously to give a corresponding cosmetic formulation an advantageous consistency in terms of conditioning and satisfactory deposition properties, for its application to the surface to be treated and/or made up, the latter property being reflected especially by good spreadability.

The deposition properties of exemplary compositions according to this invention are generally evaluated visually by depositing the compositions generally onto a body surface. Spreading should be able to be performed easily, i.e., with satisfactory slip properties, and should allow rapid access to good homogeneity of thickness of deposit over the whole of this surface.

Wax or Waxy Phase

For the purposes of the present invention, the term "wax" means a lipophilic compound with a reversible solid/liquid change of state, having a melting point of greater than or equal to 25° C., which may be up to 200° C., and having in solid form an anisotropic crystal organization. By melting the wax, it is possible to make it miscible with oils and to form a microscopically homogeneous mixture, but, by lowering the temperature of the mixture, recrystallization of the wax in the oils takes place.

Advantageously, the wax or the waxy phase employed in exemplary embodiments according to the invention has a melting point of between 25° C. and 42° C., especially between 25° C. and 40° C. and more particularly between 25° C. and 35° C.

In exemplary embodiments of this invention, the melting point corresponds to the temperature of the most endothermic peak observed by thermal analysis (DSC) as described in ISO standard 11357-3; 1999.

The melting point of the wax may be measured using a differential scanning calorimeter (DSC), for example the calorimeter sold under the name MDSC 2920 by the company TA Instruments.

The measuring protocol is as follows:

A sample of 5 mg of wax placed in a crucible is subjected to a first temperature increase ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation of the difference in power absorbed by the empty crucible and by the crucible containing the sample of wax is measured as a function of the temperature. The melting point of the compound is the temperature value corresponding to the top of the peak of the curve representing the variation in the difference in absorbed power as a function of the temperature.

As specified previously, waxes employed in exemplary embodiments of this invention are in solid form in the form of crystallites with a shape factor at least equal to 2, which may also be referred to as needle crystallites.

In general, needle crystallites are crystallites in the form of objects for which one dimension is greater than the other two. They are characterized by their shape factor, i.e., the ratio of their longest length to the greater of the other two dimensions (width, thickness). In embodiments of the present invention, this shape factor is greater than or equal to 2, in particular greater than or equal to 3, more particularly greater than or equal to 4 and especially greater than or equal to 5.

These needle crystallites and especially their dimensions may be characterized visually according to the following method.

The wax is deposited onto a microscope slide, which is placed on a hotplate. The slide and the wax are heated to a temperature generally at least 5° C. above the melting point of the wax or of the wax mixture under consideration. After melting, the liquid thus obtained and the microscope slide are allowed to cool so as to solidify. Observation of crystallites is performed using an optical microscope of Leica DMLB100 type, with an objective lens selected as a function of the size of the objects to be viewed, and in polarized light. The dimensions of the crystallites are measured using image analysis software such as that sold by the company Microvision.

Thus, crystallites employed in exemplary embodiments of the compositions according to this invention may have a mean length of between 0.1 and 50 μm, especially between 0.5 and 30 μm and in particular between 0.5 and 20 μm. The term "mean length" denotes the dimension given by the statistical particle size distribution to half the population, referred to as the D50.

The mean length of the crystallites is more particularly the determining factor for the solid water-in-oil emulsions with a high aqueous phase content especially of greater than 50% by weight relative to the total weight of the composition.

Specifically, when there is a phase dispersed in large amount, i.e., greater than 50% and possibly up to 90% by weight, the droplets of the dispersed phase are close enough together to prevent suitable structuring by the network of waxes, if these waxes are not specific in terms of size and shape factor. By virtue of their elongated shape and their size, which is generally comparable to that of the dispersed aqueous droplets, exemplary wax crystallites according to the invention may advantageously become inserted between the aqueous droplets and thus form the wax network necessary for obtaining the required mechanical properties for the emulsion.

Exemplary embodiments of this invention also include compositions in which these crystallites are combined with the wax crystallites that do not satisfy the shape factor and/or melting point and/or size criteria defined previously.

In particular, they may be crystallites that have a shape factor and/or a length in accordance with the invention, but a melting point that does not correspond to the melting range that is preferred or required according to the invention. They may also be crystallites with a shape factor different from that required according to the invention.

For the purposes of the invention, a wax that cannot be in the form of crystallites with a shape factor at least equal to 2 and/or that cannot have a melting point ranging from 25° C. to 42° C. will be denoted by the term "wax not in accordance with the invention" or "conventional wax".

In exemplary embodiments, at least one wax in accordance with the invention is present in sufficient amount in a composition to give this composition the expected texture and mechanical properties. This is what the term "effective amount" is meant to define for the purposes of the invention.

Thus, exemplary cosmetic compositions contain at least one wax in the form of crystallites in accordance with the invention in sufficient amount such that the maximum force measured by texturometry during the penetration of a probe into a sample of this wax according to the precise measuring conditions defined previously should be at least equal to 0.25 newtons and in particular at least equal to 0.30 newtons.

For example, exemplary embodiments of the compositions according to the invention may contain from 1% to 40%, especially from 2% to 20% and in particular from 4% to 10% by weight of wax in accordance with the invention.

However, for the reasons explained previously, in exemplary embodiments, the effective amount of wax incorporated in order to obtain the required hardness and the desired spreading properties is liable to vary significantly depending on the amount of continuous phase (wax and oil) and of dispersed phase (aqueous phase). Furthermore, this amount is also liable to vary depending on whether or not the composition also comprises one or more other "conventional" wax(es), and as a function of the physical parameters of these waxes, for instance hardness, and finally of their respective amounts.

According to a first variant, exemplary embodiments of compositions according to the invention may comprise 50% by weight or less than 50% by weight of aqueous phase, with the fatty phase comprising from 10% to 40% by weight, especially from 15% to 30% by weight and in particular from 15% to 25% by weight of a waxy phase, the said waxy phase comprising from 0.1% to 100% by weight of at least one wax in accordance with the invention.

According to a second variant, exemplary embodiments of compositions according to the invention may comprise more than 50% by weight of an aqueous phase, with the fatty phase possibly comprising from 10% to 40% by weight, especially from 10% to 30% by weight and in particular from 5% to 25% by weight of a waxy phase containing from 50% to 100% by weight and in particular from 70% to 100% by weight of at least one wax in accordance with the invention, and optionally from 0.5% to 50% by weight and in particular from 0.5% to 30% by weight of at least one wax not in accordance with the invention.

According to an exemplary embodiment of the invention, the waxy phase of the composition according to the invention consists of one or more wax(es) in accordance with the invention.

Waxes that are suitable for the invention may be of natural origin, especially plant, mineral, animal and/or synthetic origin. The waxes may be simultaneously of animal and synthetic origin.

They may especially be hydrocarbon-based waxes or silicone waxes.

The hydrocarbon-based waxes advantageously have a density at 25° C. of less than 0.9 and preferably less than 0.8 g/cm$^3$, preferably between 0.75 and 0.80 g/cm$^3$. They also advantageously have a molecular mass of less than 500 g/mol, preferably less than or equal to 400 g/mol, preferably between 200 and 400 g/mol and more preferably between 250 and 350 g/mol.

Non-limiting illustrations of hydrocarbon-based waxes that may be mentioned more particularly include Fischer-Tropsch waxes, which are also known as polymethylene waxes or synthetic paraffin wax. They correspond to the formula $C_nH_{2n+2}$.

According to an exemplary embodiment of the invention, the wax according to the invention is at least one polymethylene wax and in particular the wax Cirebelle 505® manufactured by the company Sasol, with a melting point equal to 40° C.

As regards the silicone waxes, it may especially be a wax of polyoxyalkylenated silicone type, i.e. a silicone comprising at least one oxyalkylene group of the type $(-C_xH_{2x}O)_a$ in which x may range from 2 to 6 and a is greater than or equal to 2.

Oxyalkylenated silicones that may be suitable for the invention may be chosen from the compounds of general formulae (I), (II), (III), (IV) and (V):

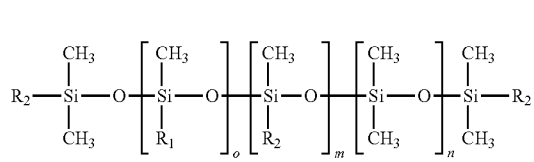

(I)

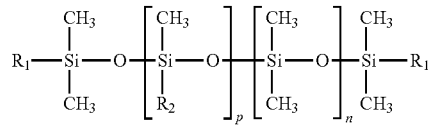

(II)

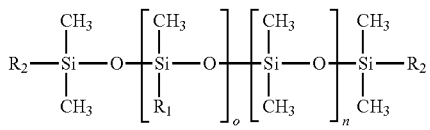

(III)

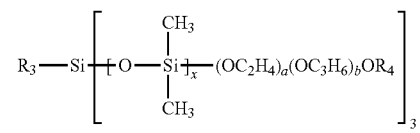

(IV)

in which formulae (I), (II), (III) and (IV):

$R_1$, which may be identical or different, represents a linear or branched $C_1$-$C_{30}$ alkyl or phenyl radical, $R_2$, which may be identical or different, represents a radical $C_cH_{2c}$—O—$(C_2H_4O)_a(C_3H_6O)_b$—$R_5$ or a radical —$C_cH_{2c}$—O—$(C_4H_8O)_a$—$R_5$, $R_3$ and $R_4$, which may be identical or different, denote a linear or branched $C_1$ to $C_{12}$ alkyl radical, and preferably a methyl radical, $R_5$, which may be identical or different, is chosen from a hydrogen atom, a linear or branched alkyl radical of 1 to 12 carbon atoms, a linear or branched alkoxy radical of 1 to 6 carbon atoms, a linear or branched acyl radical of 2 to 30 carbon atoms, a hydroxyl radical, a $C_1$-$C_6$ aminoalkoxy radical optionally substituted on the amine, a $C_2$-$C_6$ aminoacyl radical optionally substituted on the amine, an aminoalkyl radical optionally substituted on the amine and on the alkyl chain, a $C_2$-$C_{30}$ carboxyacyl radical, a group optionally substituted with one or two substituted aminoalkyl radicals, —NHCO(CH$_2$)$_d$OH, a phosphate group, -M, which may be identical or different, denotes a hydrogen atom, Na, K, Li, NH$_4$ or an organic amine, $R_7$ denotes a hydrogen atom,
d ranges from 1 to 10,
m ranges from 0 to 20,
n ranges from 0 to 500,
o ranges from 0 to 20,
p ranges from 1 to 50,
a ranges from 0 to 50,
b ranges from 0 to 50,
a+b is greater than or equal to 2,
c ranges from 0 to 4,
x ranges from 1 to 100.

Such silicones are described, for example, in U.S. Pat. No. 5,070,171, U.S. Pat. No. 5,149,765, U.S. Pat. No. 5,093,452 and U.S. Pat. No. 5,091,493.

Silicones that are most particularly suitable are those of formula (III) in which $R_2$, which may be identical or different, represents a radical $C_cH_{2c}$—O—$(C_2H_4O)_a(C_3H_6O)_b$—$R_5$, with $R_5$, a, b and c being defined as above. In this embodiment, b and c are preferably equal to 0 and a is between 1 and 50, preferably between 5 and 30 and more preferably between 10 and 20.

Waxes as defined above preferably also show an ability to crystallize in the form of crystallites with a shape factor at least equal to 2 and preferably have a melting point ranging from 25° C. to 42° C.

A non-limiting illustration of a wax of this type that may be mentioned more particularly is the wax Belsil DMC 6038® sold by the company Wacker-Belsil.

Aqueous Phase

Exemplary embodiments of the composition according to the invention include at least one aqueous medium as a dispersed phase, constituting an aqueous phase.

This aqueous phase may consist essentially of water.

It may also comprise a mixture of water and of water-miscible organic solvent (miscibility in water of greater than 50% by weight at 25° C.), for instance lower monoalcohols containing from 1 to 5 carbon atoms, such as ethanol, isopropanol, glycols containing from 2 to 8 carbon atoms, such as propylene glycol, ethylene glycol, 1,3-butylene glycol, dipropylene glycol, $C_3$-$C_4$ ketones and $C_2$-$C_4$ aldehydes.

The aqueous phase may also comprise a dispersion of hydrophobic particles, for instance polymers in dispersion. However, a person skilled in the art will take care to ensure that the introduction of polymeric thickeners does not inverse the sense of the emulsion.

This aqueous phase may, where appropriate, be thickened, gelled or structured by also incorporating therein a conventional aqueous gelling agent especially of mineral origin, for instance clay, and/or of organic origin, for instance an aqueous gelling polymer.

As mentioned previously, this aqueous phase may be present in very variable amounts in exemplary embodiments of the composition according to the invention. It preferably represents more than 50% by weight, especially more than 60% by weight, in particular more than 70% by weight, especially more than 75% by weight and more particularly more than 80%, or even more than 85% by weight, relative to the total weight of the composition.

Fatty Phase

Besides a waxy phase, exemplary embodiments of the composition according to the invention may comprise at least one fatty phase that is liquid at room temperature (25° C.) and atmospheric pressure. The fatty phase may, if necessary, also contain one or more structuring and gelling agents of oils of organic nature and/or lipophilic organic solvents.

The liquid fatty phase may be present in a proportion of from 0.5% to 80% by weight, in particular from 1% to 75% by weight, more particularly from 2% to 65% by weight, especially from 3% to 60% by weight, or even from 5% to 50% by weight, relative to the total weight of the composition according to the invention.

Exemplary embodiments of the fatty phase of the composition according to the invention may especially comprise, as liquid fatty phase, at least one liquid fatty substance of volatile or non-volatile, silicone or non-silicone oil type, or a mixture thereof.

For the purposes of the invention, the term "volatile oil" means any oil capable of evaporating on contact with the skin in less than one hour, at room temperature and atmospheric pressure. Preferred volatile oils of the invention are volatile cosmetic oils, which are liquid at room temperature, having a non-zero vapour pressure, at room temperature and atmospheric pressure, ranging from 0.01 to 300 mmHg (1.33 Pa to 40 000 Pa) and preferably greater than 0.3 mmHg (30 Pa).

The term "non-volatile oil" means an oil that remains on the skin at room temperature and atmospheric pressure for at least several hours and that especially has a vapour pressure of less than or equal to 0.01 mmHg (1.33 Pa).

These volatile or non-volatile oils may be hydrocarbon-based oils, in particular of plant or animal origin, silicone oils or mixtures thereof. The term "hydrocarbon-based oil" means an oil mainly containing hydrogen and carbon atoms and possibly oxygen, nitrogen, sulphur and/or phosphorus atoms.

Volatile hydrocarbon-based oils may be chosen from hydrocarbon-based oils containing from 8 to 16 carbon atoms, and especially branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane, and for example the oils sold under the trade names Isopars® or Permetyls®, branched $C_8$-$C_{16}$ esters such as isohexyl neopentanoate, and mixtures thereof. Other volatile hydrocarbon-based oils, for instance petroleum distillates, especially those sold under the name Shell Solt® by the company Shell, may also be used.

Volatile oils that may also be used include volatile silicones, for instance volatile linear or cyclic silicone oils, especially those with a viscosity $\leq 8$ centistokes ($8 \times 10^{-6}$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The volatile oil may be present in exemplary embodiments of the composition according to the invention in a content ranging from 0.1% to 90% by weight, especially from 1% to 50% by weight, and in particular from 2% to 35% by weight, relative to the total weight of the composition.

The non-volatile oils may be chosen especially from non-volatile hydrocarbon-based oils, which may be fluorinated, and/or non-volatile silicone oils.

Non-volatile hydrocarbon-based oils that may especially be mentioned include:

hydrocarbon-based oils of animal origin, hydrocarbon-based oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are especially wheatgerm oil, sunflower oil, grapeseed oil, sesame seed oil, maize oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, sesame seed oil, marrow oil, blackcurrant oil, evening primrose oil, millet oil, barley oil, quinoa oil, rye oil, safflower oil, candlenut oil, passionflower oil or musk rose oil; shea butter; or caprylic/capric acid triglycerides, for instance those sold by the company Stearineries Dubois or those sold under the names Miglyol 810®, 812® and 818® by the company Dynamit Nobel, synthetic ethers containing from 10 to 40 carbon atoms, linear or branched hydrocarbons of mineral or synthetic origin, such as petroleum jelly, polydecenes, hydrogenated polyisobutene such as parleam, and squalane, and mixtures thereof, synthetic esters, for instance oils of formula $R_1COOR_2$ in which $R_1$ represents a linear or branched fatty acid residue containing from 1 to 40 carbon atoms and $R_2$ represents a hydrocarbon-based chain, which is especially branched, containing from 1 to 40 carbon atoms, on condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, alcohol or polyalcohol heptanoates, octanoates, decanoates or ricinoleates, for instance propylene glycol dioctanoate; hydroxylated esters, for instance isostearyl lactate or diisostearyl malate; polyol esters and pentaerythritol esters, fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol, higher fatty acids such as oleic acid, linoleic acid or linolenic acid, and mixtures thereof, and dialkyl carbonates, the two alkyl chains possibly being identical or different, such as the dicaprylyl carbonate sold under the name Cetiol CC® by Cognis.

Non-volatile silicone oils that may be used in the composition according to the invention may be non-volatile polydimethylsiloxanes (PDMS), polydimethylsiloxanes comprising alkyl or alkoxy groups, which are pendent and/or at the end of a silicone chain, these groups each containing from 2 to 24 carbon atoms, phenylsilicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, and mixtures thereof.

The non-volatile oils may be present in exemplary embodiments of the composition according to the invention in a content ranging from 0.01% to 90% by weight, especially from 0.1% to 85% by weight and in particular from 1% to 70% by weight relative to the total weight of the composition.

Besides a wax or waxy phase in accordance with the invention, exemplary embodiments of the composition according to the invention may also comprise a wax not in accordance with the invention.

In exemplary embodiments, the composition may also comprise at least one wax other than the waxes in accordance with the invention. This may be a hydrocarbon-based wax, a fluoro wax and/or a silicone wax and may be of animal, plant, mineral or synthetic origin. It may be chosen, for example, from beeswax, carnauba wax, candelilla wax, paraffin waxes, hydrogenated castor oil, silicone waxes and microcrystalline waxes, and mixtures thereof.

Surfactant

In exemplary embodiments, the emulsion advantageously contains at least one surfactant, which may be present especially in a proportion ranging from 0.1% to 30% by weight and better still from 5% to 15% by weight relative to the total weight of the composition.

Suitable surfactants may be chosen from anionic and nonionic surfactants. Reference may be made to the document "Encyclopedia of Chemical Technology, Kirk-Othmer", volume 22, pp. 333-432, 3rd edition, 1979, Wiley, for the definition of the properties and (emulsifying) functions of surfactants, in particular pp. 347-377 of this reference, for the anionic and nonionic surfactants.

The surfactants preferably used in exemplary embodiments of the composition according to the invention are chosen from:

nonionic surfactants: fatty acids, fatty alcohols, polyethoxylated or polyglycerolated fatty alcohols such as polyethoxylated stearyl or cetylstearyl alcohol, fatty acid esters of sucrose, alkylglucose esters, in particular polyoxyethylenated $C_1$-$C_6$ alkyl glucose fatty esters, and mixtures thereof, anionic surfactants: $C_{16}$-$C_{30}$ fatty acids neutralized with amines, aqueous ammonia or alkaline salts, and mixtures thereof.

Surfactants that allow a water-in-oil emulsion to be obtained are more particularly suitable.

Surfactants for obtaining water-in-oil emulsions are surfactants whose HLB (hydrophilic-lipophilic balance) is between 3 and 6. The definition of the HLB is given in the book Galenica 5, Les Systèmes Dispersés-I Agents de Surface et Emulsions, F. Puisieux, M. Seiller, pages 153-155, published by Lavoisier.

More specifically, silicone surfactants of dimethicone copolyol or alkyl dimethicone copolyol type may be used, for instance those sold under the names Abil EM 90® and Abil WE 09® (from the company Goldschmidt) and DC3225C® and DC5200® (by the company Dow Corning).

Particulate Phase

Exemplary embodiments of the composition according to the invention may also comprise a particulate phase, which may be present in a proportion of from 0.01% to 40% by weight, especially from 0.01% to 30% by weight and in particular from 0.05% to 20% by weight relative to the total weight of the composition.

It may especially comprise pigments and/or nacres and/or fillers conventionally used in cosmetic compositions.

The term "pigments" should be understood as meaning white or colored, mineral or organic particles that are insoluble in the liquid hydrophilic phase, which are intended to color and/or opacify the composition. The term "fillers" should be understood as meaning colorless or white, mineral or synthetic, lamellar or non-lamellar particles. The term "nacres" should be understood as meaning iridescent particles produced especially by certain molluscs in their shell, or alternatively synthesized.

Pigments may be present in exemplary embodiments of the composition in a proportion of from 0.01% to 25% by weight, in particular from 0.01% to 15% by weight and especially from 0.02% to 5% by weight relative to the weight of the composition.

As mineral pigments that may be used in exemplary embodiments of the invention, mention may be made of titanium oxide, zirconium oxide or cerium oxide, and also zinc oxide, iron oxide or chromium oxide, ferric blue, manganese violet, ultramarine blue and chromium hydrate. Among the organic pigments that may be used in exemplary embodiments of the invention, mention may be made of carbon black, pigments of D & C type, and pigments based on cochineal carmine or on barium, strontium, calcium or aluminium, or alternatively the diketone pyrrolopyrroles (DPP) described in documents EP-A-542 669, EP-A-787 730, EP-A-787 731 and WO-A-96/08537.

The nacres may be present in exemplary embodiments of the composition in a proportion of from 0.01% to 25% by weight, especially from 0.01% to 15% by weight and in particular from 0.02% to 5% by weight relative to the total weight of the composition.

Nacreous pigments may be chosen from white nacreous pigments such as mica coated with titanium or with bismuth oxychloride, colored nacreous pigments such as titanium mica with iron oxides, titanium mica especially with ferric blue or with chromium oxide, titanium mica with an organic pigment of the abovementioned type and nacreous pigments based on bismuth oxychloride.

Fillers may be present in a proportion of from 0.01% to 40% by weight, especially from 0.01% to 30% by weight and in particular from 0.02% to 20% by weight relative to the total weight of the composition.

They may preferably be spherical fillers, for instance talc, zinc stearate, mica, kaolin, polyamide (Nylon®) (Orgasol® from Atochem) powders, polyethylene powders, tetrafluoroethylene polymer (Teflon®) powders, starch, boron nitride, polymer microspheres such as those of polyvinylidene chloride/acrylonitrile, for instance Expancel® (Nobel Industrie), acrylic acid copolymers (Polytrap® from the company Dow Corning), silicone resin microbeads (for example Tospearls® from Toshiba) and organopolysiloxane elastomers.

Exemplary embodiments of the composition may also comprise water-soluble or liposoluble dyes preferably in a content ranging from 0.01% to 6% by weight and especially ranging from 0.01% to 3% by weight relative to the total weight of the composition. Suitable liposoluble dyes include, for example, Sudan Red, DC Red 17, DC Green 6, β-carotene, soybean oil, Sudan Brown, DC Yellow 11, DC Violet 2, DC Orange 5 and quinoline yellow. Suitable water-soluble dyes include, for example, beetroot juice and methylene blue.

Exemplary embodiments of the composition according to the invention may also comprise any ingredient conventionally used in the fields under consideration and more especially in cosmetics and dermatology. These ingredients may in particular be chosen from vitamins, antioxidants, trace elements, softeners, sequestering agents, fragrances, basifying or acidifying agents, preserving agents, UV-screening agents, hydrophilic or lipophilic active agents, and mixtures thereof. The amounts of these various ingredients may be, for example, those conventionally used in the fields under consideration, for example from 0.01% to 20% of the total weight of the composition.

Needless to say, a person skilled in the art will take care to select this or these additional compound(s), and/or the amount thereof, such that advantageous properties of the composition according to the invention are not, or are not substantially, adversely affected by the envisaged addition.

Compositions of this invention may be obtained according to the preparation processes conventionally used in cosmetics or dermatology. More specifically, emulsions in accordance with the invention can be prepared according to protocols for preparing conventional water-in-oil emulsions.

Taking into account the presence in these wax emulsions especially of at least one wax with a melting point ranging from 25° C. to 40° C., the emulsification is generally performed at a temperature at least 5° C. above the end melting point of the highest-melting wax.

In embodiments, all of the lipid and/or liposoluble ingredients are mixed together and brought to a temperature at least 5° C. above the end melting point of the wax or waxy phase. The aqueous phase, combined with the water-soluble components, is also brought to an equivalent temperature. The aqueous phase is then gradually incorporated, generally dropwise, into the fatty phase and the mixture is homogenized with stirring, after which it is left to cool to room temperature.

Exemplary embodiments of the compositions according to the invention may be in the form of a product cast in stick or dish form, for instance lipsticks or lip balms, cast foundations, concealer products, complexion correctors and/or enhancers, eyeshadows, makeup rouges, antisun balms and deodorant balms.

This invention is illustrated by the following examples, which are merely for the purpose of illustration. Unless otherwise specified, the percentages are expressed as weight percentages and the ranges of values expressed in the form "between . . . and . . ." include the values forming the specified limits.

EXAMPLES

Seven foundation formulations in stick form are prepared according to the following protocol.

The components of the fatty phase, i.e. the waxes, oils, surfactants and pigments, are introduced into a heating pan. The mixture is brought to a sufficient temperature to melt all the waxes. This temperature is at least 5° C. above the melting point of the highest-melting wax. The components of the aqueous phase, i.e., the water, the preserving agents and the salts, are mixed together and heated (to an equivalent temperature). The aqueous phase is then added dropwise to the fatty phase, at a rate of about 20 g of water per minute, with stirring using a Rayneri machine at 400 rpm.

At the end of the addition, stirring is continued for 20 minutes at 1000 rpm. The emulsion is then cast in Laffon brand stick containers with an outside diameter of 25 mm.

The wax used in the form of crystallites in accordance with the invention is a wax sold under the name Belsil DMC 6038 by the company Wacker. It is used in tests B, D and G below.

The other tests are comparative tests, i.e., tests not incorporating wax crystallites with a shape factor at least equal to 2 in their emulsion.

|  |  | A comparative | B | C comparative | D | E comparative | F comparative | G |
|---|---|---|---|---|---|---|---|---|
| waxy phase | Hydrogenated jojoba oil (from the company Desert Whale) | 20 | 16 |  |  | 9 |  |  |
|  | Polyethylene wax (Performalene 400 Polyethylene from New Phase Technology) |  |  | 20 | 16 |  | 9 | 7 |
|  | Bis-PEG-15 methyl ether dimethicone (Belsil DMC 6038 from the company Wacker) |  | 4 |  | 4 |  |  | 2 |
| oily phase | Polydimethylsiloxane (DC 200 10 CST Fluid from Dow Corning) | 19 | 19 |  |  | 5 |  |  |
|  | Hydrogenated isoparaffin (Parleam from the company NOF Corporation) |  |  | 19 | 19 |  | 5 | 5 |
| Surfactant | Silicone surfactant (Abil WE09 from the company Goldschmidt) | 5 | 5 | 5 | 5 | 5 | 5 | 5 |
| Pigments | Yellow iron oxide | 5 | 5 | 5 | 5 | 5 | 5 | 5 |
| aqueous phase |  |  |  |  |  |  |  |  |
| Water |  | 25 | 25 | 25 | 25 | 50 | 50 | 50 |
| Glycerol |  | 25 | 25 | 25 | 25 | 25 | 25 | 25 |
| preserving agent | Methyl para-hydroxybenzoate | 0.3 | 0.3 | 0.3 | 0.3 | 0.3 | 0.3 | 0.3 |
| Salt |  | 0.7 | 0.7 | 0.7 | 0.7 | 0.7 | 0.7 | 0.7 |
| Measured hardness |  | 0.904 | 0.317 | 0.938 | 0.926 | 0.269 | 0.713 | 0.426 |

|  | A comparative | B | C comparative | D | E comparative | F comparative | G |
| --- | --- | --- | --- | --- | --- | --- | --- |
| Formulation in stick form | possible | possible | possible | possible | too soft, impossible | possible | possible |
| Appearance of deposit | little | large | little | large | — | very little | large |

The quality of the deposit is assessed comparatively after making a single application to the forearm; a sufficiently large deposit is desired, since it gives a visible color on the skin.

Only the three tests according to the invention, i.e., B, D and G, make it possible simultaneously to obtain a stick of suitable texture and a satisfactory deposit, with, in the case of test G, a large amount of aqueous phase.

While this invention has been described in conjunction with the exemplary embodiments and examples outlined above, various alternatives, modifications, variations, improvements and/or substantial equivalents, whether known or that are or may be presently unforeseen, may become apparent to those having at least ordinary skill in the art. Accordingly, the exemplary embodiments of the invention, as set forth above, are intended to be illustrative, not limiting. Various changes may be made without departing from the spirit and scope of the invention. Therefore, the invention is intended to embrace all known or later developed alternatives, modifications, variations, improvements and/or substantial equivalents.

What is claimed is:

1. A cosmetic composition in the form of a water-in-oil solid emulsion comprising an aqueous phase dispersed in a fatty phase, wherein:
    the fatty phase comprises at least one wax and at least one liquid fatty oil, the wax having a melting point of between 25° C. and 42° C., the wax being in solid form in the form of crystallites having a shape factor of at least 2 and a mean length of between 20 and 50 µm;
    the wax is present in the composition in an amount of from 2 to 4% by weight; and
    the wax is at least one polyoxyalkylenated silicone according to formula III

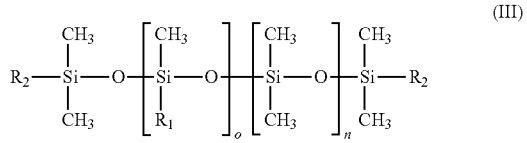

wherein:
    $R_1$ is independently a linear or branched $C_1$-$C_{30}$ alkyl or phenyl radical;
    $R_2$, each of which are identical or different, represents a radical $C_cH_{2c}$—O—$(C_2H_4O)_a(C_3H_6O)_b$—$R_5$;
    $R_5$ is a methyl group;
    n ranges from 1 to 500;
    o is 0;
    a ranges from 1 to 50;
    b is 0; and
    c is 0.

2. The cosmetic composition of claim 1, wherein the crystallites have a shape factor of at least 3.

3. The cosmetic composition of claim 1, wherein the crystallites have a shape factor of at least 4.
4. The cosmetic composition of claim 1, wherein the crystallites have a shape factor of at least 5.
5. The cosmetic composition of claim 1, wherein the wax has a melting point of from 25° C. to 40° C.
6. The cosmetic composition of claim 1, wherein the wax has a melting point of from 25° C. to 35° C.
7. The cosmetic composition of claim 1, wherein the crystallites have a mean length of from 20 to 30 µm.
8. The cosmetic composition of claim 1, wherein the composition comprises more than 70% by weight of the aqueous phase.
9. The cosmetic composition of claim 1, wherein the composition comprises more than 75% by weight of the aqueous phase.
10. The cosmetic composition of claim 1, wherein the composition comprises more than 80% by weight of the aqueous phase.
11. The cosmetic composition of claim 1, wherein the fatty phase comprises from 10% to 40% by weight of a waxy phase containing from 0.1% to 100% by weight of the wax.
12. The cosmetic composition of claim 1, wherein the fatty phase comprises from 15% to 30% by weight of a waxy phase containing from 0.1% to 100% by weight of the wax.
13. The cosmetic composition of claim 1, wherein the fatty phase comprises from 10% to 40% by weight of a waxy phase containing from 50% to 100% by weight of the wax.
14. The cosmetic composition of claim 1, wherein the fatty phase comprises from 10% to 30% by weight of a waxy phase containing from 50% to 100% by weight of the wax.
15. The cosmetic composition of claim 1, wherein the fatty phase comprises from 5% to 25% by weight of a waxy phase containing from 50% to 100% by weight of the wax.
16. The cosmetic composition of claim 1, wherein the fatty phase comprises from 10% to 40% by weight of a waxy phase containing from 70% to 100% by weight of the wax.
17. The cosmetic composition of claim 1, wherein the fatty phase comprises from 10% to 30% by weight of a waxy phase containing from 70% to 100% by weight of the wax.
18. The cosmetic composition of claim 1, wherein the fatty phase comprises from 5% to 25% by weight of a waxy phase containing from 70% to 100% by weight of the wax.
19. The cosmetic composition of claim 1, wherein the composition comprises from 0.5% to 80% by weight of at least one liquid fatty phase relative to the total weight of the composition.
20. The cosmetic composition of claim 1, wherein the composition comprises from 1% to 75% by weight of at least one liquid fatty phase relative to the total weight of the composition.
21. The cosmetic composition of claim 1, wherein the composition comprises from 2% to 65% by weight of at least one liquid fatty phase relative to the total weight of the composition.

22. The cosmetic composition of claim 1, wherein the composition comprises from 3% to 60% by weight of at least one liquid fatty phase relative to the total weight of the composition.

23. The cosmetic composition of claim 1, wherein the composition is in the form of a product cast in stick or dish form.

24. The cosmetic composition of claim 1, wherein the composition is in at least one form selected from the group consisting of lipsticks, lip balms, cast foundations, concealer products, complexion correctors or enhancers, eyeshadows, makeup rouges, antisun balms and deodorant balms.

25. A method for preparing a cosmetic composition in the form of a water-in-oil solid emulsion, comprising dispersing an aqueous phase in a fatty phase to form a water-in-oil solid emulsion, wherein:
the fatty phase comprises at least one wax having a melting point of between 25° C. and 42° C. as a texturing agent, the at least one wax being in solid form in the form of crystallites having a shape factor of at least 2 and a mean length of between 20 and 50 μm;
the wax is present in the composition in an amount of from 2 to 4% by weight; and
the wax is at least one polyoxyalkylenated silicone according to formula III

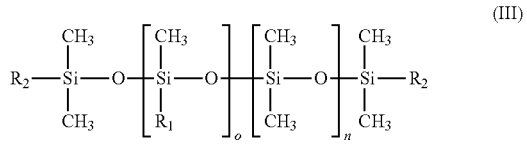

wherein:
$R_1$ is independently a linear or branched $C_1$-$C_{30}$ alkyl or phenyl radical;
$R_2$, each of which are identical or different, represents a radical $C_cH_{2c}$—O—$(C_2H_4O)_a(C_3H_6O)_b$—$R_5$;
$R_5$ is a methyl group;
n ranges from 1 to 500;
o is 0;
a ranges from 1 to 50;
b is 0; and
c is 0.

26. A method for preparing a cosmetic composition in the form of a water-in-oil solid emulsion containing more than 50% by weight of an aqueous phase, comprising dispersing the aqueous phase in a fatty phase to form the water-in-oil solid emulsion, wherein:
the fatty phase comprises at least one wax having a melting point of between 25° C. and 42° C. as a texturing agent, the at least one wax being in solid form in the form of crystallites having a shape factor of at least 2 and a mean length of between 20 and 50 μm;
the wax is present in the composition in an amount of from 2 to 4% by weight; and
the wax is at least one polyoxyalkylenated silicone according to formula III

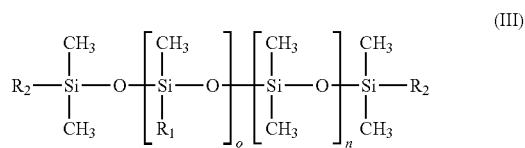

wherein:
$R_1$ is independently a linear or branched $C_1$-$C_{30}$ alkyl or phenyl radical;
$R_2$, each of which are identical or different, represents a radical $C_cH_{2c}$—O—$(C_2H_4O)_a(C_3H_6O)_b$—$R_5$;
$R_5$ is a methyl group;
n ranges from 1 to 500;
o is 0;
a ranges from 1 to 50;
b is 0; and
c is 0.

27. A cosmetic process for caring for and/or making up skin and/or lips, comprising applying the composition of claim 1 to the skin and/or the lips.

28. The cosmetic composition of claim 1, wherein the at least one liquid fatty oil is a volatile silicone oil.

29. The cosmetic composition of claim 1, wherein the composition comprises a surfactant selected from the group consisting of non-ionic surfactants, anionic surfactants, and silicone surfactants.

* * * * *